United States Patent [19]

Jamiolkowski et al.

[11] Patent Number: 4,889,119
[45] Date of Patent: Dec. 26, 1989

[54] SURGICAL FASTENER MADE FROM GLYCOLIDE-RICH POLYMER BLENDS

[75] Inventors: Dennis D. Jamiolkowski, Long Valley; Mark T. Gaterud, Annandale; Hugh D. Newman, Jr., Chester; Shalaby W. Shalaby, Lebanon, all of N.J.

[73] Assignee: Ethicon, Inc., Somerville, N.J.

[*] Notice: The portion of the term of this patent to May 3, 2005 has been disclaimed.

[21] Appl. No.: 146,014

[22] Filed: Jan. 20, 1988

Related U.S. Application Data

[63] Continuation-in-part of Ser. No. 755,888, Jul. 17, 1985, Pat. No. 4,741,337.

[51] Int. Cl.$^4$ .............................. A61B 17/04
[52] U.S. Cl. .................... 606/220; 128/325; 128/326; 525/415; 528/354
[58] Field of Search .............. 128/334 R, 325, 326; 525/410, 415; 528/354; 523/113

[56] References Cited

U.S. PATENT DOCUMENTS

| | | | |
|---|---|---|---|
| 3,892,821 | 7/1975 | Koleske et al. | 260/860 |
| 4,052,988 | 10/1977 | Doddi et al. | 128/335.5 |
| 4,060,089 | 11/1977 | Noiles | 128/325 |
| 4,137,921 | 2/1979 | Okuzumi et al. | 128/335.5 |
| 4,402,445 | 9/1983 | Green | 227/19 |
| 4,428,376 | 1/1984 | Mericle | 128/335 |
| 4,534,350 | 8/1985 | Golden et al. | 128/334 C |
| 4,646,741 | 3/1987 | Smith | 128/335.5 |
| 4,671,280 | 6/1987 | Dorband et al. | 128/334 C |
| 4,741,337 | 5/1988 | Smith et al. | 128/334 C |
| 4,744,365 | 5/1988 | Kaplan et al. | 128/335.5 |

FOREIGN PATENT DOCUMENTS

WO/8401-508-A 4/1984 World Int. Prop. O.

Primary Examiner—Richard J. Apley
Assistant Examiner—Paul Prebilic
Attorney, Agent, or Firm—Charles J. Metz

[57] ABSTRACT

There is described a surgical fastener comprising a glycolide-rich blend of two or more polymers, one polymer being a high lactide content polymer and another being a high glycolide content polymer. The blend as a whole contains from about 65 to 85 weight percent polymerized glycolide, with the high glycolide content polymer constituting at least 50 weight percent of the blend.

12 Claims, 15 Drawing Sheets

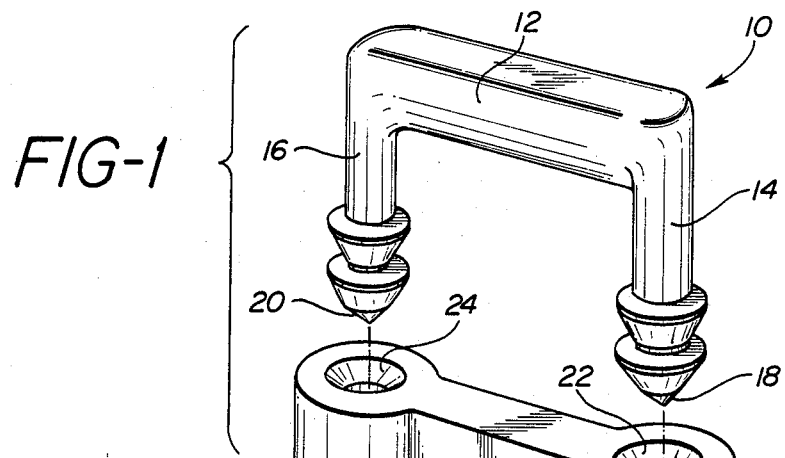
FIG-1
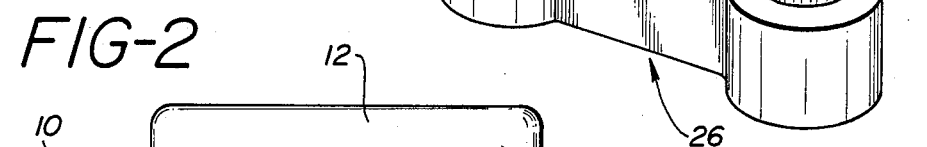
FIG-2
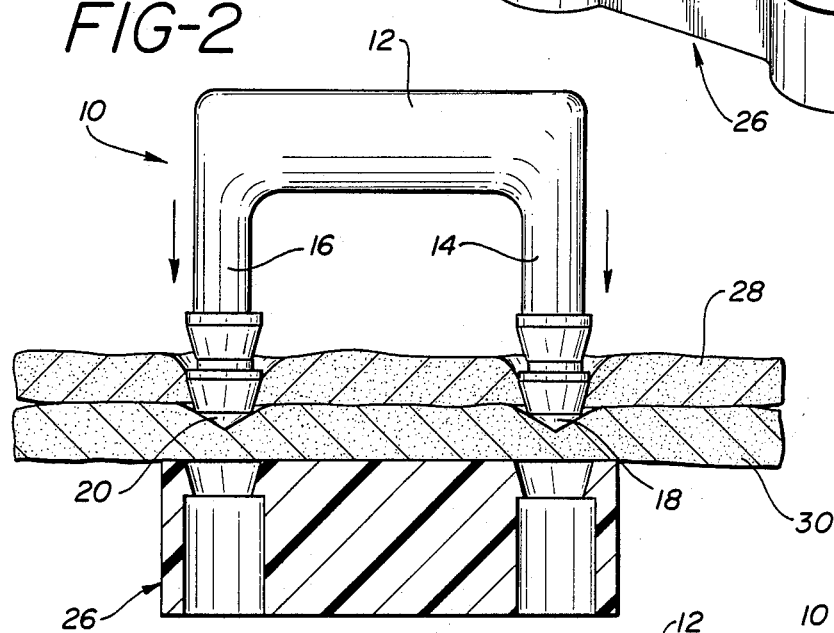
FIG-3
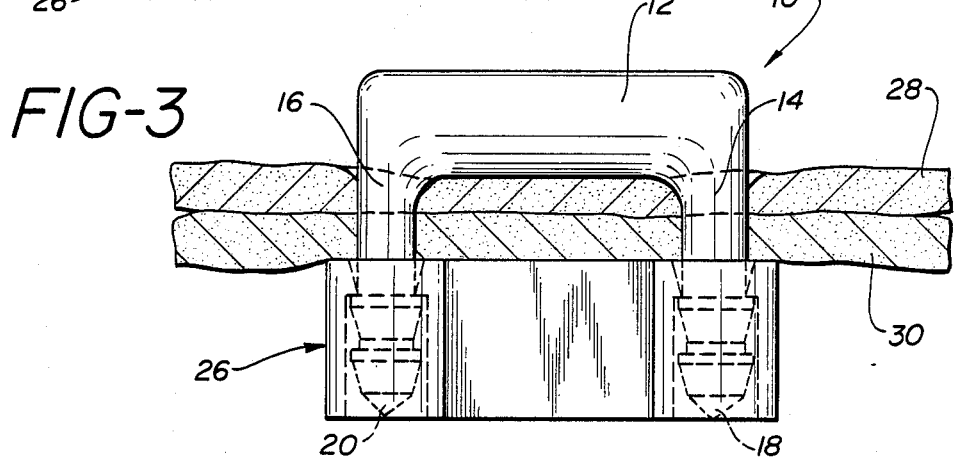

SURGICAL FASTENER MADE FROM GLYCOLIDE-RICH POLYMER BLENDS

This application is a continuation-in-part of application Ser. No. 755,888, filed July 17, 1985 now U.S. Pat. No. 4,741,337.

The invention relates to an absorbable surgical fastener such as a ligating clip or a surgical staple of the staple/receiver type, made from glycolide-rich blends of polymers.

BACKGROUND OF THE INVENTION

Surgical staples and ligating clips are beginning to come into wide use in the surgical profession as an alternative to sutures and ligatures. One advantage of clips and staples in comparison with sutures and ligatures is that tissue fastening or ligating with a staple or clip, whether applied singly or as an array applied in a row or in a ring, is much simpler and faster than with a suture or a ligature. Surgical procedures can be speeded up, thereby reducing the length of time the patient must be anesthetized and shortening the operating room time. Thus, there are both medical and economic reasons for the shift to staples and clips from sutures and ligatures.

The first surgical staples to be used, and still the majority being used, were metal staples. But metal staples, when used externally, must be removed, with accompanying patient discomfort. And when metal staples are used internally, they are left in place. While the metal staples are tiny and become encapsulated by natural processes, and (except in a few cases, some of which will be discussed below) little or no difficulty has been associated with such staples left in the patient, for internal applications surgeons would prefer to use absorbable materials that eventually disappear after their usefulness has ended. For this reason, there is a substantial incentive to develop an absorbable plastic surgical staple.

It appears to be out of the question to produce an absorbable plastic surgical staple of reasonable size that fastens simply by bending back on itself in a manner analogous to the way metal staples fasten. The available absorbable plastics simply lack the required combination of ductility and stiffness that would be required for this purpose. For this reason, the initial attempts to produce an acceptable absorbable plastic surgical staple has concentrated on the staple/receiver type of fastener. In this type of fastener, a staple member includes a cross-piece or base and one or more attached legs which are designed to pierce the tissue to be fastened and to enter receptacles in the receiver on the other side of the tissue. The receiver holds the leg(s) tightly, with the tissue being held between the cross-piece or base and the receiving member. The desirable characteristics of such a fastener are the following:

(1) adequate stiffness in the legs to pierce the tissue without being deflected in such a way that they fail to meet the receptacles in the receiver;
(2) adequate strength in the receiver to hold the legs;
(3) strength retention in vivo for a period which may vary from about three to six weeks, depending on the function of the fastener;
(4) dimensional stability at moderately elevated temperatures, e.g., up to 65° C., so that the fastener will not warp when exposed to such temperatures, which are commonly encountered during shipping or storage in warm weather;
(5) sterilizability; and
(6) ability to be totally absorbed or at least non-palpable within a reasonable period of time.

It has not proven to be an easy matter to obtain the requisite combination of properties. For instance, early designs of absorbable surgical staples utilized temporary metal reinforcement for the fastener legs during insertion of the staple to insure adequate stiffness. For instance see Noiles, U.S. Pat. No. 4,060,089 and Green, U.S. Pat. No. 4,402,445. An absorbable clip and an absorbable staple (both of which have been used commercially) were made from an 80/20 lactide/glycolide (mol/mol) copolymer. These fasteners have the disadvantage that they are dimensionally unstable when heated to temperatures over 120° F. (49° C.). Therefore, care must be taken in handling these fasteners, because temperatures well over 120° F. are commonly encountered in shipping and storage in the U.S. during the warmer months.

Later commercial surgical staples are made from either of two blends of lactide and glycolide polymers such that in each case the blend has much greater than 50 percent lactide-based moieties. Specifically, one blend had an overall lactide/glycolide ratio of 71/29, by weight, and the other, 64/36, by weight. These staples (as well as the fasteners mentioned in the previous paragraph) persist for rather a long time in vivo because of their high lactide content. Also, for a long time before these staples disappear from the body, they are hard, palpable, and brittle. When they fail, it is by brittle failure such that hard fragments are formed; such fragments have a potential for causing discomfort or even tissue damage.

Absorbable ligating clips made from poly(p-dioxanone) have recently been introduced commercially. Metallic ligating clips have been used for some time.

In one type of surgery, some problems have been found with the use of metal surgical staples. A report entitled "Unusual Complications Following Abdominal Hysterectomy: Dyspareunia and Consort Glans Laceration After Vaginal Cuff Stapling", which appeared in the Journal of the Maine Medical Association, Vol. 71, June 1980, pages 169–170, related the following:

A line of metal surgical staples had been used to seal off the vaginal cuff during an abdominal hysterectomy. The patient complained of leukorrhea, dyspareunia, and post coital bleeding after the operation. Slight injury to her consort was also reported. The problem was found to be caused by the surgical staples that had been used during the hysterectomy. After removal of the staples (some of them had to be removed surgically), the problems disappeared.

Beresford has reported similar experiences with metallic staples used to seal the vaginal cuff during abdominal hysterectomy. (Ref.—"Automatic Stapling Techniques in Abdominal Hysterectomy", Surgical Clinics of North America, Vol. 64, No. 3, June 1984, pages 609–618.) For this reason, the use of absorbable staples in this type of operation would be highly desirable. Beresford (op. cited, supra) and McTammany ("Vaginal Cuff Closure During Abdominal Hysterectomy Using Absorbable Staples:, The Berks County Medical Record, Volume 77, February 1986, pages 35–36) have reported the use of absorbable staples in this procedure. It is believed that the staples used were the high lactide content staples discussed above. No traumatic problems of the type encountered with metallic staples have been reported with the use of these absorbable staples. However, Beresford reported that the line of absorbable staples can be palpated in the vaginal vault until they absorb. The time to complete absorption is reported to be of the order of 180 days. He also reported that some staple shedding occurred and that the staples appeared in the vaginal vault in some patients after 2 to 4 weeks. McTammany reported that in most of his patients in which the absorbable staples were used, white fragments of the row of staples could be seen after 4 to 6 weeks, and that the fragments crumbled when grasped by forceps.

This invention provides an absorbable surgical fastener, such as a surgical staple, a ligating clip, an anastomotic coupler, a fascia closure, or the like, that has an overall composition containing more than 50 percent of polymerized glycolide, and provides, unexpectedly, a highly desirable combination of properties. With such a high glycolide content, one would have expected the subject devices to have limited strength retention in vivo, since molded polyglycolide (homopolymer and high glycolide content copolymer) staples have an unacceptable strength retention profile in that they lose their strength in too short a period of time for most surgical uses. (Coworkers of the inventors herein have discovered that highly oriented, crystalline polyglycolide surgical devices made from extruded rods or filaments which have been shaped and then annealed while under restraint so as to prevent shrinkage, have significantly longer strength retention in vivo then molded devices made from the same polyglycolide polymers. However, the process for producing such devices is much more involved and expensive than simple molding. See U.S. Pat. No. 4,671,280 for a description of such highly oriented, crystalline devices.) However, the staples and other devices of this invention do retain a substantial proportion of their initial strength during the critical wound healing period, and only a short time (a few weeks) after the fasteners of the invention have served their purpose, they rapidly soften so that they become impalpable within about six to ten weeks after implantation.

BRIEF SUMMARY OF THE INVENTION

This invention provides a surgical fastener comprising a glycolide-rich blend of polymers. The blend contains two or more polymers, one being a high lactide content polymer and another being a high glycolide content polymer. The blend as a whole contains from about 65 to about 85 weight percent polymerized glycolide, with the high glycolide content polymer constituting at least 50 weight percent of the blend.

In one preferred aspect of the invention there is provided a surgical staple comprising:
(a) a staple member including a base member and at least one pointed leg member extending substantially perpendicularly from said base member; and
(b) a receiving member including an aperture arranged and constructed to receive and retain the free end of said leg member,
wherein said staple member comprises the glycolide-rich blend of polymers of the invention, and wherein said receiving member comprises an absorbable polymer, such as poly(p-dioxanone) or a glycolide-rich blend of polymers.

In another preferred aspect, the invention provides a hemostatic ligating clip comprising said glycolide-rich blend of polymers.

Among the advantages of the invention are the ability to injection mold the parts made from the blend of the invention, and the fact that the parts retain measurable strength for a long enough time after implantation to perform the required task, and yet, in a preferred embodiment of the invention, the parts become soft and impalpable within about six to ten weeks after implantation in living tissue. This latter feature (i.e., the combination of rapid softening after having retained sufficient strength to perform the intended function) is a truly valuable and unexpected advantage.

THE PRIOR ART

Green, in U.S. Pat. No. 4,402,445, discloses absorbable surgical staples made from, inter alia, "an amorphous copolymer of 10-50% (by weight) glycolide and 50-90% lactide..." and from "...polymers of p-dioxanone..." Noiles, in U.S. Pat. No. 4,060,089, discloses the preparation of surgical staples from polyglycolic acid and polylactic acid.

Mericle, in U.S. Pat. No. 4,428,376, discloses the preparation of surgical staples from homopolymers and copolymers of lactide, glycolide, and p-dioxanone.

Golden et al., in U.S. patent application Ser. No. 359,443, filed Mar. 18, 1982, discloses an absorbable staple in which the fastening member is made from "an absorbable polymer of glycolide and lactide" and the receiving member is made from poly((p-dioxanone). The said Golden et al. application is assigned to the same assignee as this application.

Doddi et al., in U.S. Pat. No. 4,052,988, disclose surgical devices made from poly(p-dioxanone).

World patent application WO8401-508-A describes absorbable surgical fasteners made from copolymers containing 70-85 mole percent lactide and 15-30 mole percent glycolide.

Okuzumi et al., in U.S. Pat. No. 4,137,921, disclose certain copolymers of lactide and glycolide, and that such copolymers can be used to make various surgical devices.

Koleske et al., in U.S. Pat. No. 3,892,821, disclose homogeneous blends of certain polymers using cyclic ester polymers (e.g., polycaprolactone) as additives to impart homogeneity to the blend.

BRIEF DESCRIPTION OF THE DRAWINGS

FIG. 1 is an exploded perspective view of a staple/receiver type surgical staple useful in the invention;

FIG. 2 is a front view of the staple of FIG. 1 in the act of fastening tissue;

FIG. 3 is a front view of the staple of FIG. 1 in place holding tissue together;

DETAILED DESCRIPTION OF THE INVENTION

Figure 4:
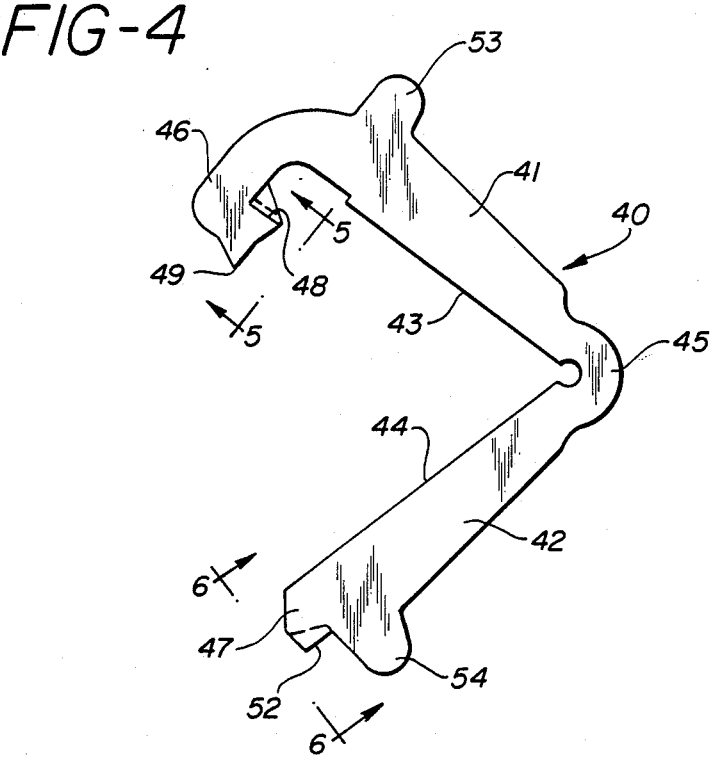
FIG. 4 is a perspective view of a ligating clip useful in the invention.

The invention resides in the use in a surgical fastener of a blend of at least two polymers, the overall blend being rich in polymerized glycolide.

The blend of polymers used in the invention is glycolide rich, that is, the blend as a whole contains from about 65 to about 85 weight percent polymerized glycolide. At least one of the polymers in the blend is polyglycolide homopolymer or a predominantly glycolide copolymer containing, e.g., at least about 90 mole percent glycolide, the remainder being lactide. This glycolide rich polymer is present in the blend in proportions of at least 50 weight percent. Also, at least one of the polymers in the blend is polylactide homopolymer or a predominantly lactide copolymer containing, e.g., at least 50, preferably at least 65, and more preferably at least 75, mol percent lactide, the remainder being glycolide or another copolymerizable monomer such as p-dioxanone that will form absorbable/bidegradable polymerized units in the copolymer. The two or more polymers used in the blend are used in such proportions that, overall, the blend contains from about 65 to about 85 weight percent of polymerized glycolide.

The polymers used in the invention are known materials. For instance, they are disclosed in U.S. Pat. to Schnieder (No. 3,797,499), Salzberg (No. 2,758,987), Schmitt et al. (No. 3,739,773), and Bezwada et al. (No. 4,643,191). As a rule, the lactide homopolymers and lactide-rich copolymers will have molecular weights such that they have inherent viscosities of from about 1 to 3 and preferably about 1.5 to 1.9, dl/gm, tested at 25° C. at a concentration of 0.1 gm/dl in hexafluoroisopropyl alcohol ("HFIP"). The glycolide homopolymers and glycolide-rich copolymers are easier to characterize by melt index than by inherent viscosity because of their poor solubility in organic solvents. They usually have melt index values of from about 0.1 to about 0.9, and preferably from about 0.2 to about 0.6, gram per 10 minutes. The melt index is determined by the procedure described in ASTM D-1238-79 (a thoroughly dried sample of polymer is employed), using a 26 mil die orifice, a weight of 3700 grams plus the 100-gram piston weight, at a temperature of 235° C. The melt index is the weight of polymer taken during the interval from 15 to 16 minutes after beginning the test, multiplied by 10.

Poly(p-dioxanone), one preferred polymer for use in the receiver member of a surgical staple of the staple/receiver type, is also a known material. Its nature and preparation are described, for instance, in Doddi et al., U.S. Pat. No. 4,052,988. Poly(p-dioxanone) having an inherent viscosity of from about 1.2 to about 2.2, and preferably about 1.6 to 1.9, dl/gm, tested at 25° C. and a concentration of 0.1 gm/dl in HFIP, is normally used in the receiver. A blend of the invention may also be used as the receiver.

Any of the polymers used in the invention can contain dyes so as to make the surgical fasteners of the invention easier to visualize against the surgical field.

In one preferred aspect, the invention provides a surgical staple of the staple/receiver type wherein the staple member is made from a blend of the invention and the receiver is made from an absorbable polymer, such as poly(p-dioxanone) or a blend similar to or the same as that used in the staple member.

The staple can be made by injection molding of the two parts using injection molding procedures that are analogous to those that are well known in the art. For example, the staple member, which is made of a blend of two or more polymers, can be injection molded at temperatures within the range of from about 215° C. to about 225° C. at an injection molding pressure of, for example, 1650 to 1750 psi. (These conditions are typical for the 70/30 polyglycolide/polylactide blend disclosed in the Examples below.) These conditions are also used if the blend is used as the receiver. Typically, the feed for the injection molder will be a melt blend of the polymers in pellet form, although a dry mix of the polymers in finely divided form (pellets or granular—the several polymers in the dry mix should be in a similar physical form and size so that they will not segregate during handling) can be fed to the injection molding machine, provided sufficient mixing in the injection molding machine occurs. The receiver member, when made of poly(p-dioxanone), can be injection molded at a temperature within the range of from about 105° C. to about 120° C., at a pressure of, for example, about 1350 to 1450 psi. The polymers should be quite dry when being injection molded in order to avoid hydrolytic degradation during processing. After molding, the staple can be packaged and sterilized by conventional procedures. It is recommended that the polymers be handled so as to minimize premature hydrolytic degradation or thermal degradation. Thus, the polymers should be stored dry before molding, the molding operation should be dry, and the molded parts should be stored dry. Also, residence time during processing should be kept to a minimum so as to minimize thermal and shear degradation.

FIGS. 1–3 show a typical surgical staple of the invention. The staple member 10 includes a base 12 and two legs 14,16 extending generally perpendicularly from the base 12. Each leg 14,16 has a pointed end 18,20 that is capable of piercing tissue. The legs 14,16 are arranged and constructed so as to snap fit into the receptacles 22,24 of a receiver 26. In a typical use, layers 28,30 of tissue to be fastened are positioned between the staple member 10 and the receiver 26. The legs 14,16 of the staple member 10 are driven through the layers 28,30 of tissue, as shown in FIG. 2, until the ends of the legs 14,16 snap fit in the receptacles 22,24 in the receiver 26, to thereby hold the tissue securely between the staple member 10 and receiver 26, as is shown in FIG. 3. The design of staple member and receiver shown in the Figures is merely illustrative. Other designs can be used, if desired.

In another preferred aspect of the invention, there is provided a hemostatic ligating clip comprising the blend of the invention. The advantages of the clip comprising the blend of the invention compared to clips made wholly of poly(p-dioxanone) are the following:
(a) more rapid absorption by the body; and
(b) the blend is stiffer, so a clip made from the blend would more readily be able to penetrate tissue.

Referring to the drawings (FIGS. 4-9), there is shown a clip 40 that can be used in the invention. As depicted in FIG. 4 the clip comprises a pair of leg members 41 and 42 having opposed vessel clamping surfaces 43 and 44. The leg members are connected at their proximal ends by a resilient hinge portion 45.

Figure 5:
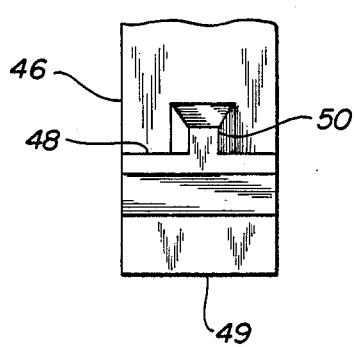
FIG. 5 is a front view taken along line 5—5 of FIG. 4.
Figure 6:
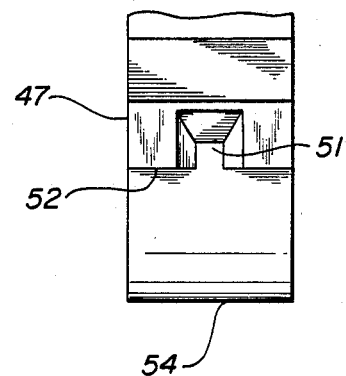
FIG. 6 is a front view taken along line 6—6 of FIG. 4.

The distal end of one of the leg members terminates in a return bend hook portion 46. The opposite leg member is somewhat shorter and terminates at its distal end in a portion 47 which can be grasped by the hook portion. The end of this leg member is angled at an obtuse angle to the vessel clamping surface. This angle aids in deflecting the hook portion as the two leg members are brought together about the hinge and allows the hook portion to deflect and then accept the leg member in the area between the inner surface 48 of the hook portion and the vessel clamping surface 43 of the opposite leg member. The hook portion includes a sharpened pointed end 49 extending from the hook portion and positioned to lead the hook portion or precede the hook portion as the clip is being closed. As shown in FIG. 5, the hook portion has a protrusion 50 disposed from the central portion of its inner surface 48. This protrusion fits into the recess 51 (see FIG. 6) positioned in the outer surface 52 of the opposite leg member 42. The protrusion and recess interlock when the clip is closed to prevent lateral movement of the leg members. The outside surfaces of the leg members each include a cylindrical boss 53 and 54 for use in holding the clip in a suitable instrument and applying the clip from said instrument as will hereinafter be described.

Figure 7:
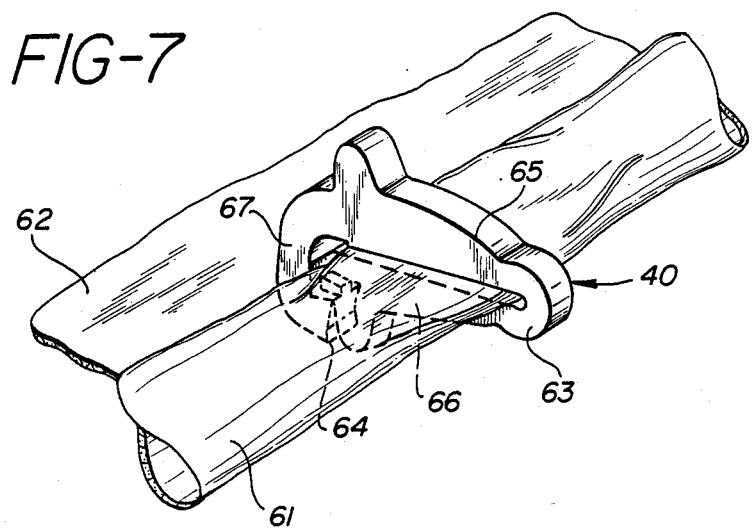
FIG. 7 is a perspective view of the clip depicted in FIG. 4 in a closed position about a blood vessel.
Figure 8:
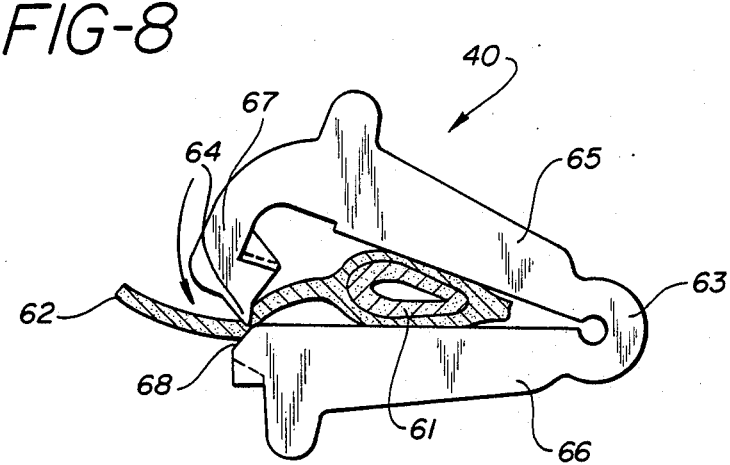
FIG. 8 is a side view of the clip of FIG. 4 immediately prior to the clip being closed about a vessel to be ligated.
Figure 9:
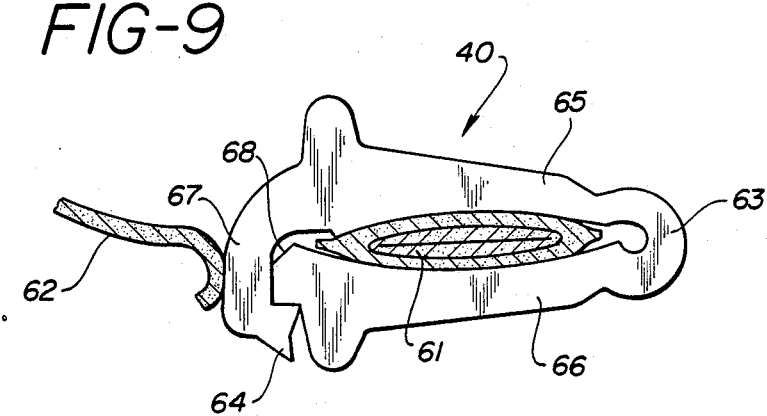
FIG. 9 is a side view of the clip of FIG. 4 with the clip in the fully closed position.
Figure 11:
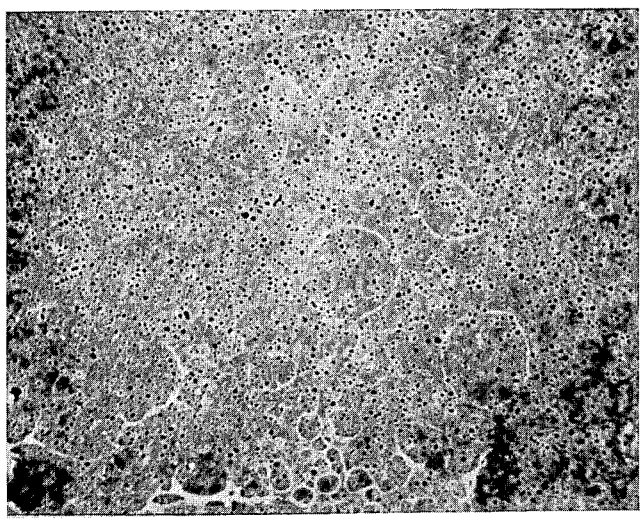
FIGS. 11–29 are photomicrographs taken at 1000× magnification of sections of staples made from blends of the invention which have been selectively extracted with solvent to remove the lactide polymer component from the blend.
Figure 12:
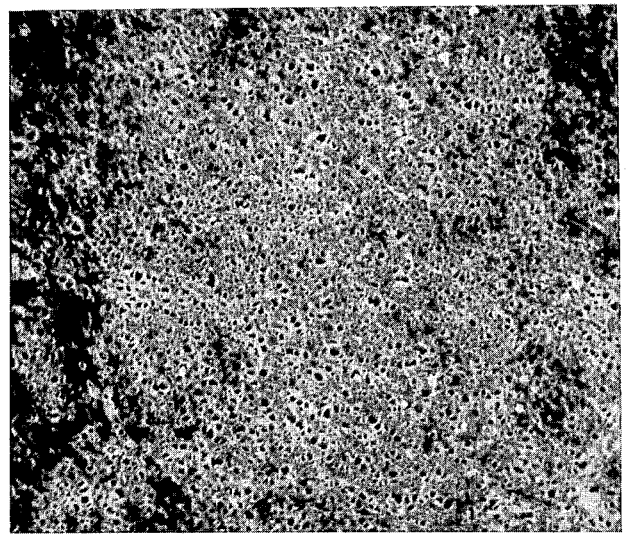
Figure 13:
Figure 14:
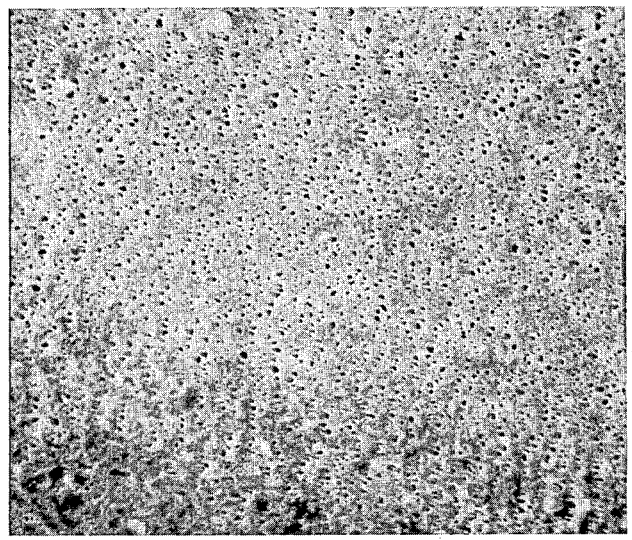
Figure 15:
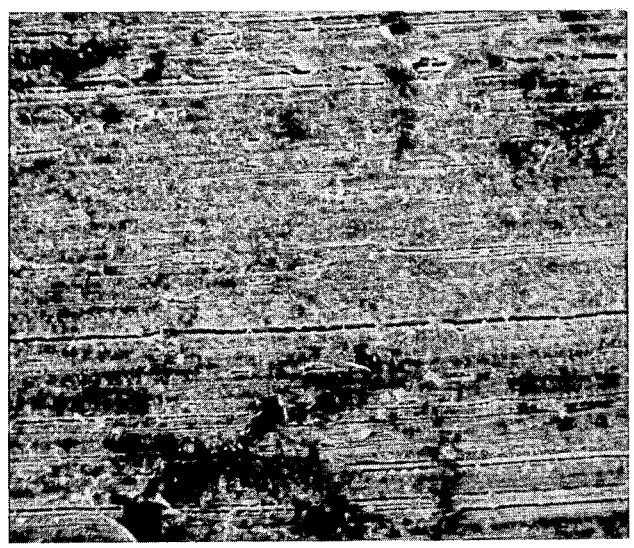
Figure 16:
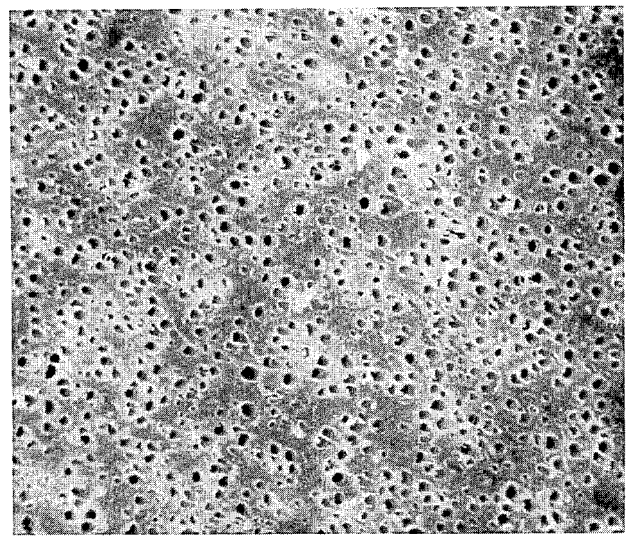
Figure 17:
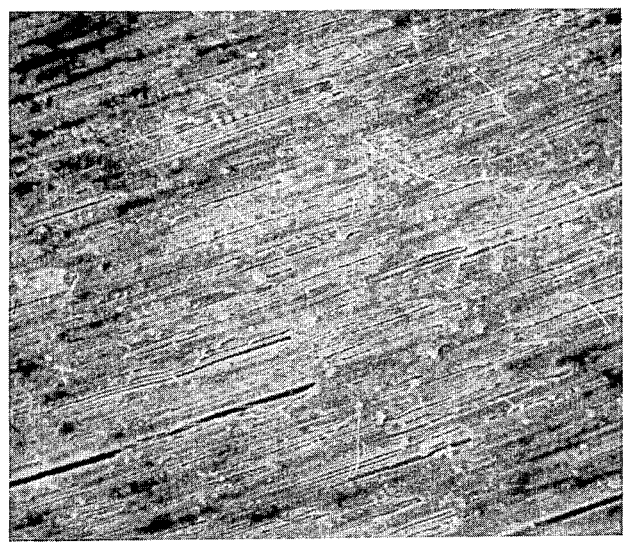
Figure 18:
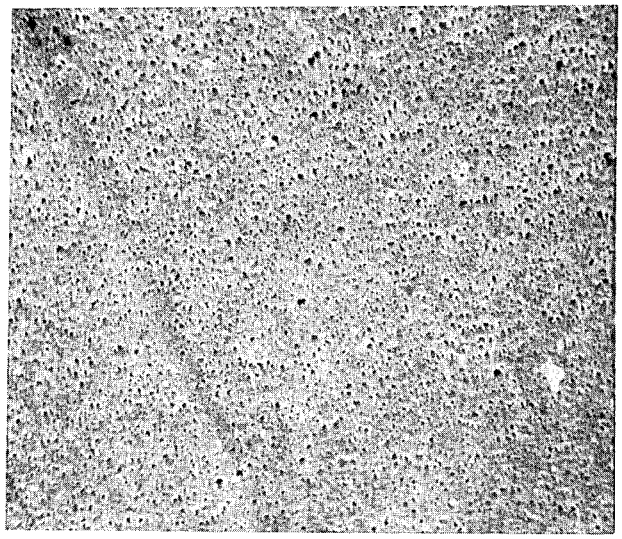
Figure 19:
Figure 20:
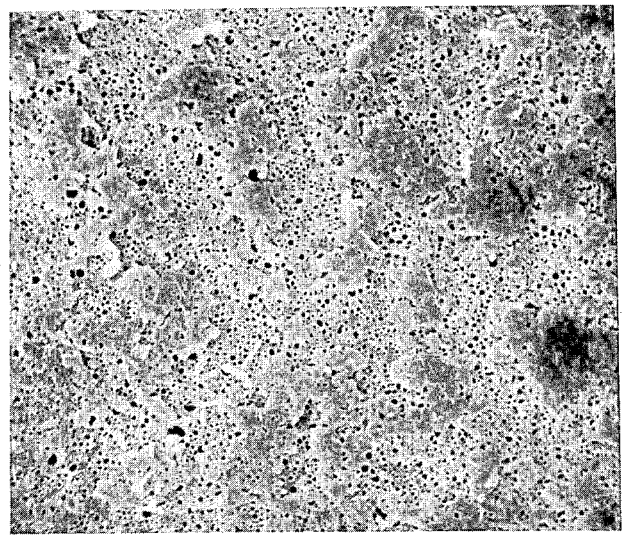
Figure 21:
Figure 22:
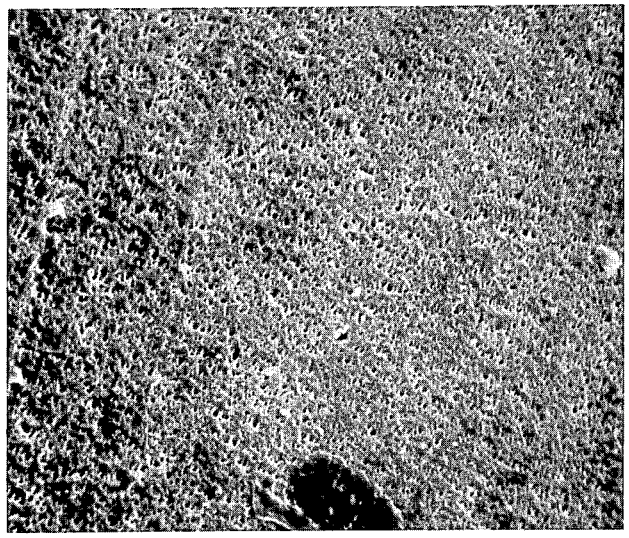
Figure 23:
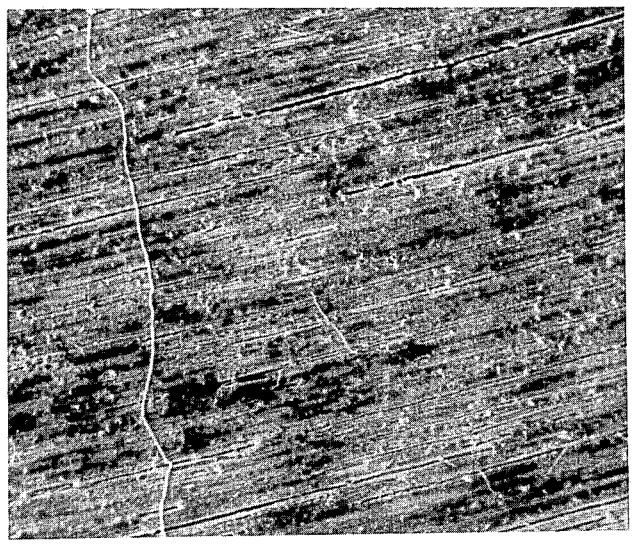
Figure 24:
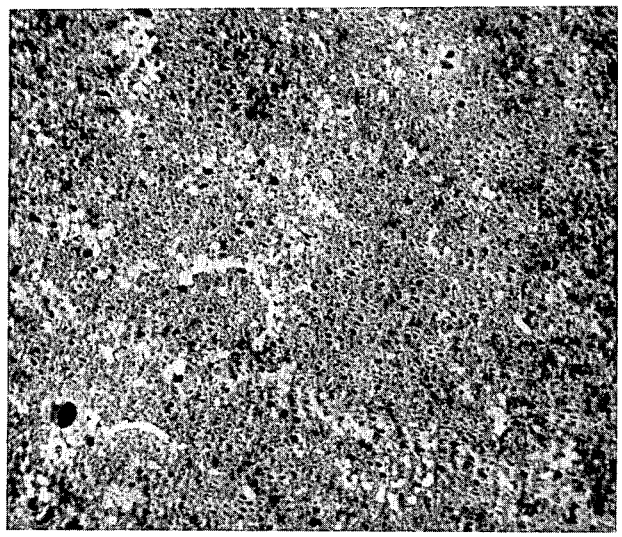
Figure 25:
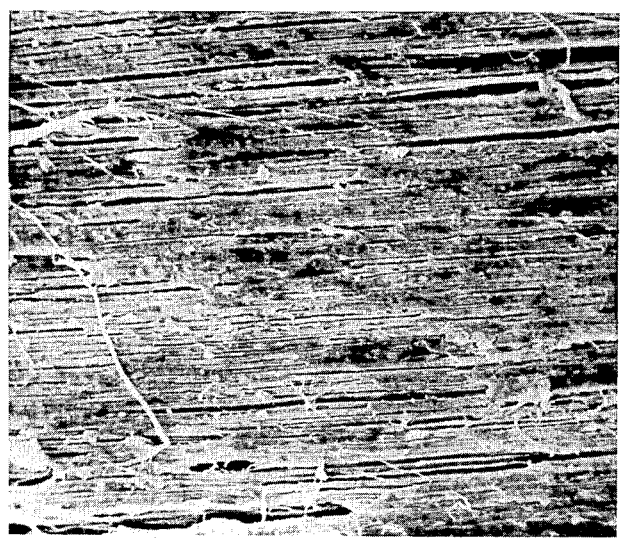
Figure 26:
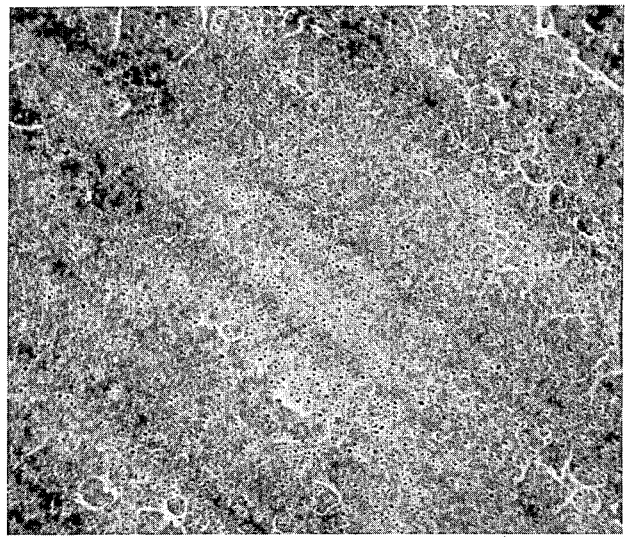
Figure 27:
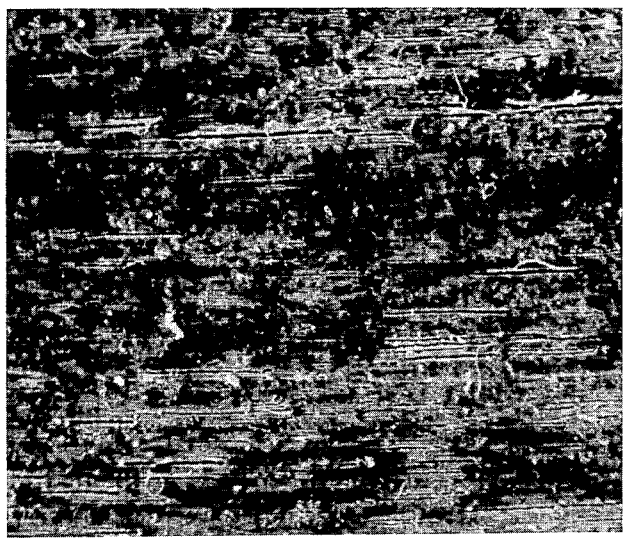
Figure 28:
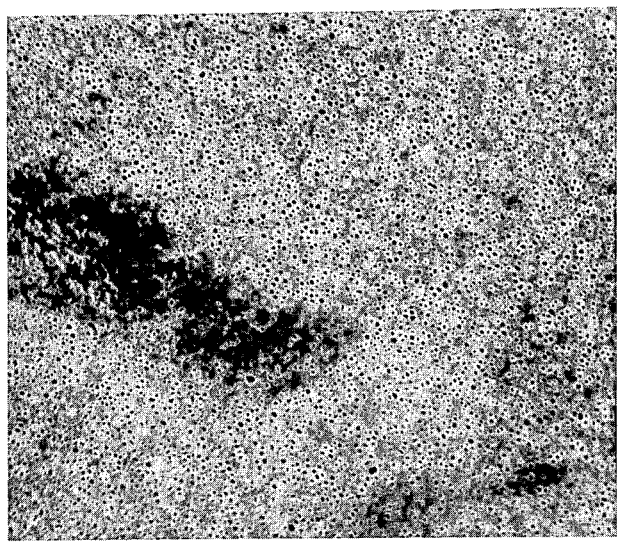
Figure 29:
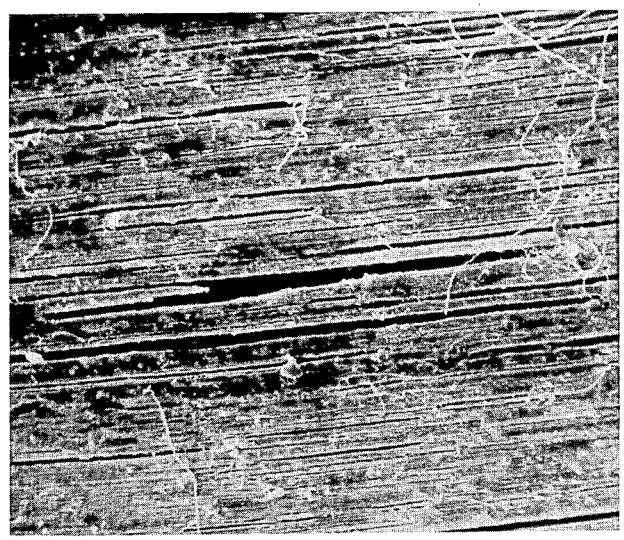

As may be more clearly seen in FIGS. 7, 8, and 9, when the clip 40 is clamped about a vessel 61 to be closed, assuming that the vessel has not been fully dissected from the surrounding connective tissue 62 (such as would be found in the mesentary), the vessel clamping surfaces are placed on opposite sides of the vessel and the leg members urged together about the resilient hinge. The penetrating sharpened end 64 of the one leg member 65 will pinch and scrape the connective tissue between itself and the camming surface 68 of the other leg member 66. This scraping action enhances the tissue penetrating ability of the sharpened end. Once the tissue is penetrated the usual sequence of closure takes place. As the leg members are urged closer together the leg member 66 continues to deflect the hook portion 67 and becomes engaged by the leg member 65, thereby locking the clip in place about the vessel without tissue interference with latch security. Though in the embodiment shown the penetrating means is a sharpened beveled end, the penetrating means may have other configurations such as a pointed end tapered at a plurality of sides, a pointed end, a plurality of pointed ends, etc.

Figure 10:
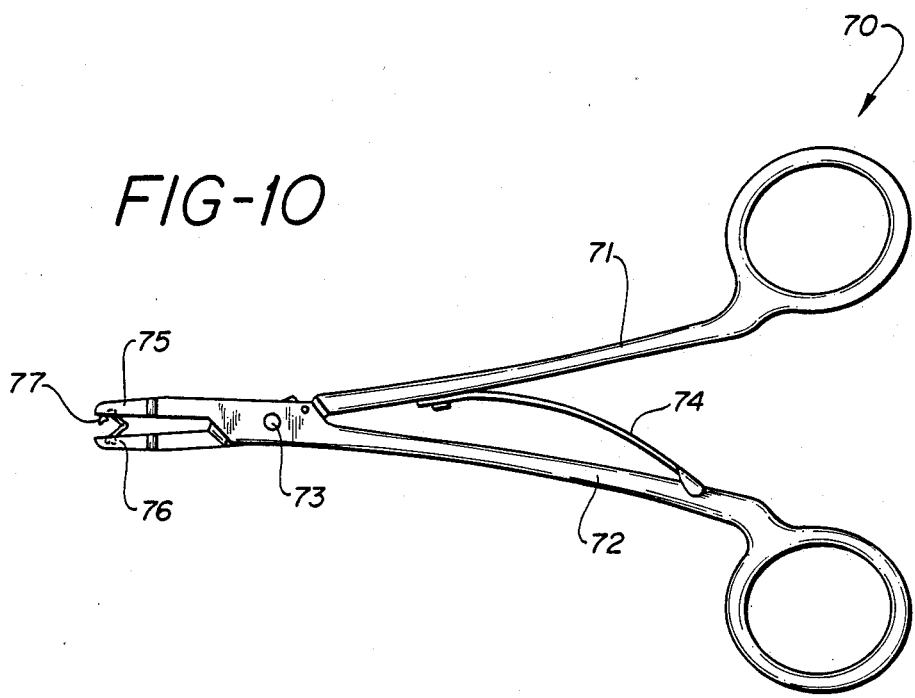
FIG. 10 is a side view of one type of instrument that may be used in applying the clip of FIG. 1.

In FIG. 10, there is shown a simplified drawing of an instrument for applying the clip described above. This instrument 70 comprises a pair of handles 71 and 72 which are connected at a hinge point 73. The handles are biased with respect to one another by a spring 74. One of the handles extends beyond the hinge point in a first jaw member 75 and the opposite handle extends beyond the hinge point in a complementary second jaw member 76. The instrument engaging means comprises cylindrical bosses (53, 54 in FIG. 4) extending from the back surfaces of the leg members of the clip 77. These bosses fit into recesses in the jaws of the instrument.

The clip is placed in the jaws with the cylindrical bosses in the appropriate recesses. The vessel clamping surfaces of the clip are then placed on opposite sides of the vessel to be closed and the instrument handles urged together closing and locking the clip about the vessel and shutting off the vessel.

The clip can be injection molded by the procedure set forth above with respect to the staple member of the surgical staple of the invention.

After injection molding, the parts made of the blend of the invention can be annealed under controlled conditions to enhance dimensional stability at elevated temperature. (By "controlled conditions" is meant that the rate of increase of temperature and the maximum temperature used in the annealing cycle are carefully controlled.) The annealing usually increases the degree of crystallinity. Polyglycolide homopolymer and glycolide-rich copolymers often develop crystallinity in the mold, and this degree of crystallinity may be sufficient in some cases. The parts made from the blend of the invention usually exhibit about 15 to about 45 percent crystallinity, measured by X-ray diffraction. The annealing, which is preferably done in a vacuum or under an inert atmosphere such as dry nitrogen, can be carried out at about 50° to 140° C., and preferably at about 60° C. to 80° C., for at least one hour. An annealing time of about 2 to 20 hours is preferred. In particular cases, the optimum annealing conditions can readily be determined experimentally.

EXAMPLE 1

Surgical staples having the design shown in FIGS. 1-3 were made by injection molding. The receivers were all made from poly(p-dioxanone) having an inherent viscosity of 1.6-1.8 in HFIP. The staple members were made from a blend of 70 parts by weight of polyglycolide homopolymer having a melt index ("MI") of 0.291, and 30 parts by weight of polylactide homopolymer having an inherent viscosity ("IV") in HFIP of 1.78. The lactide rich polymers reported in the examples herein were all made using L(−)lactide; however, other stereo configurations of lactide can be used in the invention.

Prior to injection molding, the polymers, in granular form, were dried under vacuum for a period of two weeks. They were dry mixed and fed to the injection molding machine as a dry mix. (Preferably, the polymers are mixed prior to the drying step in order to minimize the effects of any pick up of moisture that might occur in the mixing procedure.) Dryness was maintained during molding by using a dry nitrogen purge in the hopper of the injection molding machine. After molding, the samples were scoured with an organic solvent (isopropyl alcohol) to remove mold release agents and other surface contaminants, as is standard in the art. The samples were then maintained under vacuum or under a dry nitrogen purge until they were tested. The fasteners were annealed at 60° C. for 16 hours after molding.

The fasteners of the invention maintain measurable holding strength in vivo for a period of time sufficient to enable joined tissue to heal. This is illustrated by the fact that in vitro testing in phosphate buffer, pH=7.27, at 37° C., of the fasteners reveals that the force to separate the receiver from the staple member is still measurable after 21 days.

The procedure for testing the separation force is the following:

An Instron Tensiometer is set as follows:

| Crosshead speed | 0.5 inch/minute |
|---|---|
| Chart speed | 5.0 inches/minute |
| Gauge length | 1.5 inches. |

Full scale load as follows:

| Time in days | Full Scale Calibrations |
|---|---|
| 0 | 10 pounds |
| 7 | 5 pounds |
| 14 | 5 pounds |
| 21 | 2 pounds |
| 28 | 2 pounds |

The staple members are inserted in the receivers, leaving a slight gap to simulate the space taken up by tissue, and are then placed in the phosphate buffer at 37° C. The samples are tested initially and after 7, 14, 21, and 28 days.

The separation force is measured by engaging the cross piece (e.g., part 12 in FIG. 1) of the staple member with a tab of an Instron test fixture, and pulling against a strip of polyester film that has been bent around the receiver by passing it through the gap between crosspiece of the staple member and the receiver. (The polyester film is cut so that it is just narrow enough to fit through said gap.) Typical initial separation forces vary from about 8 to 9 pounds, and typical separation forces after 21 days in phosphate buffer at 37° C. are from one half to one pound, depending on the overall composition in the blend.

After 42 days in vitro, the devices made from the blend described above are so soft that they would be expected to be impalpable after 42 days in vivo. It is unusual and unexpected that an implanted device would have measurable strength after three weeks in vivo, but then after only another three weeks be so soft as to be impalpable. In general, the fasteners of the invention will be impalpable after six to ten weeks in vivo. (It is worth noting here that it is only the parts made of the subject polymer blends that so rapidly become soft and impalpable. When parts made of the subject blends are used in combination with parts made of other polymers, such as a polydioxanone receiver for a staple of the staple/receiver type, the polydioxanone receiver does not soften as rapidly as the staple portion made from the blend of the invention.)

EXAMPLES 2-3 AND CONTROLS 1-4

A series of surgical fasteners of the staple/receiver type were molded by the procedure described above in Example 1 (except that the polymers constituting the blends of Examples 2 and 3 were melt blended and granulated prior to charging to the injection molding machine—the polymers constituting the blend of Example 1 had been dry blended). The fasteners were immersed in phosphate buffered saline at 37° C., with the force required to separate the staple from the receiver being measured after 0, 14, 21, 28, and 42 days. The separation force test is described above in Example 1, and the fasteners were all substantially the same as described in connection with FIGS. 1-3. The receivers were all made of poly(p-dioxanone), and the staple portions were made from either lactide/glycolide copolymers or blends of glycolide polymers with lactide polymers. The polymers used in the staple portions of the fasteners in the first series of experiments were as follows:

Example 2—Blend of 70 weight percent polyglycolide homopolymer (MI=0.472) and 30 weight percent polylactide homopolymer (IV=1.91) Control 1—Block copolymer of 70.7 weight percent glycolide and 29.3 weight percent lactide (MI=0.034 and IV=1.60)

Example 3—Blend of 75 weight percent polyglycolide homopolymer (MI=0.472) and 25 weight percent of an 85/15 (by mol) lactide/glycolide copolymer (IV=1.63) (overall glycolide/lactide weight ratio in the blend is about 78.1/21.9)

Control 2—Block copolymer of 73.5 weight percent glycolide and 26.5 weight percent lactide (MI=0.079 and IV=1.67)

The block copolymers were made by a process similar to the process taught by Okuzumi et al. in U.S. Pat. No. 4,137,921. The difference from the specific teachings of Okuzumi et al. was that the monomer charges for the first stage of the polymerization contained a higher proportion of lactide than that specifically taught by Okuzumi et al., and the monomer charges for the second stage of the polymerization contained no lactide. With respect to Control 1, the monomer charge for the first stage was 100% lactide, and with respect to Control 2, the monomer charge in the first stage contained 91.8% (weight %) lactide and 8.2% glycolide. Okuzumi more specifically teaches that the initial charge will contain 60–90% lactide and that the second stage of the polymerization reaction will contain 10–30% lactide, the remainder of the monomer charge being glycolide in both stages.

The results of the tests are displayed below in four tables.

| | (70/30 Blend) Separation Force (lbs)[a] | | | | |
|---|---|---|---|---|---|
| Sample No | Day 0 | Day 14 | Day 21 | Day 28 | Day 42 |
| 1 | 6.309 | 2.680 | 1.125 | 0.680 | 0.332 |
| 2 | 5.990 | 2.190 | 1.155 | 0.825 | 0.557 |
| 3 | 5.820 | 2.780 | 1.190 | 0.762 | 0.287 |
| 4 | 6.350 | 2.330 | 1.080 | 0.744 | 0.344 |
| 5 | 6.520 | 2.438 | 1.065 | 0.665 | 0.362 |
| 6 | 6.759 | 2.395 | 1.024 | 0.646 | 0.376 |
| Overall Average | 6.291 | 2.469 | 1.107 | 0.720 | 0.376 |

[a]Values given in this table and in the following three tables represent averages of the results of multiple tests, usually eight to ten. The differences between each series of tests (i.e., Sample Nos.) were in the molding conditions. With respect to the molding conditions of the staples referred to in this table, the barrel temperatures were 213° C. (except for Sample 3 in which it was 232° C.), the back pressures were 360 psi in all cases, the mold temperatures were 110° C. for all samples except for Sample 6, in which the mold temperature was 80° C. The cycle times (in seconds) were as follows:
Sample 1 - 52
Sample 2 - 22
Sample 3 - 67
Sample 4 - 37
Sample 5 - 67
Sample 6 - 37

| | (71/29 Block Copolymer) Separation Force (lbs) | | | | |
|---|---|---|---|---|---|
| Sample No | Day 0 | Day 14 | Day 21 | Day 28 | Day 42 |
| 1 | 6.57 | 1.31 | 0.7 | 0.5 | 0.4 |
| 2 | 7.46 | 0.82 | 0.6 | 0.4 | 0.3 |
| 3 | 7.51 | 0.88 | 0.5 | 0.4 | 0.3 |
| 4 | 6.48 | 1.35 | 0.7 | 0.4 | 0.3 |
| 5 | 7.29 | 1.23 | 0.6 | 0.5 | 0.3 |
| 6 | 6.79 | 1.20 | 0.7 | 0.5 | 0.3 |
| 7 | 8.04 | 1.10 | 0.8 | 0.4 | 0.2 |
| 8 | 7.42 | 1.00 | 0.7 | 0.4 | 0.3 |

-continued

| (71/29 Block Copolymer) Separation Force (lbs) | | | | | |
|---|---|---|---|---|---|
| Sample No | Day 0 | Day 14 | Day 21 | Day 28 | Day 42 |
| 9 | 6.95 | 1.10 | 0.6 | 0.4 | 0.4 |
| Overall Average | 7.168 | 1.11 | 0.66 | 0.43 | 0.31 |

The mold temperatures for all samples were 110° C., except for Samples 7 and 8, whose mold temperatures were 50° and 80° C., respectively, the barrel temperatures were 206° C. except for Sample 9–216° C.), the back pressures were 360 psi (except for Sample 2–840 psi), and the cycle times were all 37 seconds except for Samples 4 and 6, which were 42 and 66 seconds, respectively.

| (78/22 Blend) Separation Force (lbs) | | | | | |
|---|---|---|---|---|---|
| Sample No | Day 0 | Day 14 | Day 21 | Day 28 | Day 42 |
| 1 | 7.309 | 1.525 | 0.847 | 0.527 | 0.409 |
| 2 | 7.400 | 1.810 | 0.914 | 0.533 | 0.260 |
| 3 | 7.569 | 2.035 | 1.008 | 0.423 | 0.207 |
| 4 | 8.190 | 1.870 | 0.912 | 0.556 | 0.209 |
| 5 | 7.569 | 1.585 | 0.745 | 0.430 | 0.285 |
| 6 | 6.930 | 1.674 | 0.892 | 0.493 | 0.248 |
| 7 | 7.720 | 1.829 | 0.821 | 0.406 | 0.157 |
| 8 | 7.959 | 1.854 | 0.982 | 0.513 | 0.278 |
| Overall Average | 7.580 | 1.773 | 0.890 | 0.487 | 0.257 |

The mold temperatures were 110° C. except for Samples 2 and 6, which were 80° C., the back pressure was 360 psi in all cases, the barrel temperature was 210° C. in all cases, and the cycle times were 37 seconds except for Samples 3 and 7, which were 67 seconds. Samples 1–4 were not annealed; samples 5–8 were annealed for one hour at 90° C. under dry nitrogen.

| (73.5/26.5 Block Copolymer) Separation Force (lbs) | | | | | |
|---|---|---|---|---|---|
| Sample No | Day 0 | Day 14 | Day 21 | Day 28 | Day 42 |
| 1 | 6.7 | 0.960 | 0.307 | 0.179 | 0.176 |
| 2 | 7.1 | 0.923 | 0.247 | 0.322 | 0.2 |
| 3 | 6.8 | 0.900 | 0.323 | 0.305 | 0.2 |
| 4 | 7.8 | 0.935 | 0.352 | 0.253 | 0.1 |
| 5 | 8.0 | 0.954 | 0.240 | 0.244 | 0.1 |
| 6 | 7.7 | 0.862 | 0.271 | 0.136 | 0.1 |
| 7 | 7.6 | 0.840 | 0.307 | 0.270 | 0.2 |
| 8 | 6.7 | 1.064 | 0.342 | 0.220 | 0.2 |
| 9 | 5.7 | 0.903 | 0.298 | 0.362 | 0.1 |
| Overall Average | 7.12 | 0.927 | 0.299 | 0.255 | 0.153 |

The mold temperatures were 110° C., except for Samples 5 and 6 which were 50° and 80° C., respectively, the cycle times were 37 seconds, except for Samples 7 and 8, which were 42 and 67 seconds, respectively, the back pressure was 360 psi, except for Sample 2 which was 840 psi, and the barrel temperatures were 213° C., except for Samples 8 and 9, which were 211° and 215° C., respectively.

The data presented above illustrates one advantage of the fasteners of the invention, which are made of blends of polymers, over fasteners made from block copolymers having similar overall glycolide to lactide ratios. The separation strength after 21 days is important because it can take up to about three weeks for a healing wound to develop most of its strength, especially in an elderly or immuno-compromised patient, and it is noted that the staples made from the blends of the invention have significantly higher separation strength after 21 days in phosphate buffered saline than do staples made from block copolymers having similar overall glycolide to lactide ratio.

The differences displayed above between the blends of the invention and block copolymers having similar overall glycolide to lactide ratio are important. However, another important difference between the staples made from the blends of the invention, on the one hand, and from block copolymers, on the other, resides in the physical changes that occur in the staples as they are absorbed or degraded within the body. As the staples of the invention are absorbed/degraded within the body, they become soft. The consistency of the absorbing staples has been described in different terms by different observers, but some of the terms that have been used include "the consistency of wet tissue paper", "soft and fibrous", and other expressions of similar import. In contrast, staples made from copolymers (both block and random copolymers) having similar glycolide to lactide ratios become brittle as they are absorbed/degraded within the body. As a result, they remain palpable within the body and they have the tendency to form fragments. Such fragments are hard and brittle, and have the potential to cause discomfort or even tissue damage in some cases. In the case of Control 1, the staples were brittle upon palpation after 28 days in vitro. The staples of Control 2 were brittle starting at 21 days in vitro and continuing throughout the 42 day test period, in contrast to the softening that occurs with the staples of this invention. The staples made from the blends of the invention do not exhibit brittleness; they begin to soften from about three to six weeks after implantation, depending upon the specific composition of the blend.

Random copolymers are even less useful than block copolymers. First, molded parts made from lactide/glycolide random copolymers of the proportions contemplated herein (i.e., from 65 to 85 weight percent glycolide) cannot be annealed outside the mold cavity if they possess even a small amount of orientation because they lack sufficient dimensional stability (owing to low crystallinity) to be subjected to even moderately elevated temperatures. Attempts to increase crystallinity by controlled annealing would not work because such random copolymers cannot be crystallized to more than a limited degree without distorting. While they can be annealed in the mold cavity, the cycle times would be impractically long for commercial production. Second, and more importantly, parts made from such random copolymers lose their strength rapidly in the in vitro test (and would be expected to perform similarly in vivo), and therefore would not retain their strength long enough after implantation to be useful for most surgical applications. This is illustrated by the experimental data set forth below.

Two lactide/glycolide random copolymers were evaluated. Control 3 (MI=0.366, IV=1.37) contained 23.7 weight % (20 mol %) lactide, the remainder being glycolide, and Control 4 (MI=0.363, IV=1.42) contained 29.3 weight % (25 mol %) lactide, the remainder being glycolide. The in vitro separation strengths of surgical staples of the staple/receiver type wherein the staple portions were made from these random copolymers (the receivers were made from polydioxanone)

were as displayed in the table below (each value given was the average of several samples, typically 8 to 10 samples).

| Control | Mold Temperature °C. | Separation Force, Pounds Days in Phosphate Buffered Saline | | | | | | |
|---|---|---|---|---|---|---|---|---|
| | | 0 | 7 | 14 | 21 | 28 | 35 | 42 |
| 3 | 20 | 8.86 | 2.09 | 0.01 | 0 | — | — | — |
| 3 | 50 | 7.66 | 2.17 | 0.01 | 0 | — | — | — |
| 3 | 110 | 7.36 | 2.57 | 0.26 | 0 | — | — | — |
| 4 | 20 | 9.18 | 1.49 | 0 | — | — | — | — |
| 4 | 50 | 8.84 | 3.67 | 0.04 | 0 | — | — | — |
| 4 | 110 | 7.58 | 2.09 | 0.10 | 0 | — | — | — |

It was noted that the staples of both Controls 3 and 4 were brittle after 21 days in vitro. They began to soften after 28 days.

The staples of Controls 3 and 4 were unacceptable because of the almost total loss of strength after only 14 days. (These staples were not annealed after molding because their low crystallinity would have caused distortion if annealing had been attempted.)

The random copolymers were made by charging the entire amount of both monomers to the reaction vessel at the beginning of the reaction, along with a suitable catalyst and initiator, and carrying out the polymerization reaction at a sufficiently high temperature to ensure essentially complete copolymerization of the monomers.

While the invention has been described most specifically in terms of a surgical staple or a hemostatic ligating clip, other types of surgical fasteners can be made from the blend of the invention. Such fasteners inlcude fascia closures and anastomotic couplers.

It is believed that the valuable combination of properties (i.e., strength retention for a period of time sufficient for the part to perform its intended tissue holding function, followed by rapid softening) exhibited by the surgical fasteners made from the subject blends is caused, to a significant degree, by the fact that the blends used in the invention are mixtures of incompatible polymers with the result that the blends exhibit segregated polymeric domains. The blends used in the invention have been found to be compositions wherein a continuous phase of glycolide polymer (polyglycolide homopolymer or high glycolide content copolymer) contains discrete domains of lactide polymer.

Evidence of the non-homogenous nature of the blends used in the invention can be seen in the photomicrographs that are shown as FIGS. 11–29. These photomicrographs show enlarged sections of devices (molded staples—made by a process similar to that described in Example 1 except that the polymers constituting the blends were melt blended and granulated prior to injection molding) made from the subject blends, wherein the staples have been extracted with either methylene chloride or chloroform. These solvents are known solvents for high lactide content polymers. Therefore, the solvent extraction selectively extracts the lactide polymer from the blends. The voids in the photomicrographs indicate where the lactide polymer domains had been prior to the extraction step.

The photomicrographs were taken with an optical microscope at 1000× magnification. They show sections that are perpendicular to the direction of flow in the mold ("X-sections") and sections that are parallel to the direction of polymer flow in the mold ("long sections"). The long section photomicrographs show that the polylactide domains are elongated, thus apparently acting to reinforce the continuous polyglycolide matrix in a manner analogous to the way that fibrous fillers reinforce a plastic matrix. This probably accounts for the desirable level of strength retention for approximately three weeks after implantation. The rapid softening that occurs thereafter is probably the joint effect of the blend being non-homogeneous and the continuous phase being a glycolide polymer that absorbs/degrades rapidly in vivo.

The blends that were used in making the staples are indicated below, along with the identification of the Figures (unless otherwise indicated, all of the polyglycolide homopolymers used were 50/50 mixtures of two batches of polymer having MI's of 0.242 and 0.206):

Blend A—30/70 (by weight) mixture of polylactide homopolymer ("PLA") (IV=1.69) and polyglycolide homopolymer ("PGA") (MI=0.229);

Blend B—35/65 (by weight) PLA/PGA mixture (PLA IV=1.69);

Blend C—25/75 (by weight) PLA/PGA mixture (PLA IV=1.69);

Blend D—20/80 (by weight) PLA/PGA mixture (PLA IV=1.69; PGA was a 13.53/8.43/78.04 mixture of three batches having MI's of 0.242, 0.206, and 0.229, respectively);

Blend E—36.4/63.5 (by weight) mixture of a copolymer of 95 mol% lactide and 5 mol% glycolide ("95/5 L/G") (IV=1.68) and PGA, giving an overall polymerized lactide to glycolide ("L/G") weight ratio in the blend of 35/65;

Blend F—31.27/68.73 (by weight) (95/5 L/G)/PGA mixture, giving an L/G weight ratio of 30/70 (L/G copolymer IV=1.68);

Blend G—26.1/73.9 (by weight) (95/5 L/G)/PGA mixture, giving an L/G weight ratio of 25/75 (L/G copolymer IV=1.68);

Blend H—38.1/61.9 (by weight) (90/10 L/G)/PGA mixture, giving an L/G weight ratio of 35/65 (L/G copolymer IV=1.48);

Blend I—27.2/72.8 (by weight) (90/10 L/G)/PGA mixture, giving an L/G weight ratio of 25/75 (L/G copolymer IV=1.48); and Blend J—32.7/67.3 (by weight) (90/10 L/G)/PGA mixture. giving an L/G weight ratio of 30/70 (L/G copolymer IV=1.48).

The Figure Numbers of the photomicrographs are identified as follows:

| Blend | Figure Numbers | |
|---|---|---|
| | X-Section | Long Section |
| A | 11 | — |
| B | 12 | 13 |
| C | 14 | 15 |
| D | 16 | 17 |
| E | 18 | 19 |
| F | 20 | 21 |
| G | 22 | 23 |
| H | 24 | 25 |
| I | 26 | 27 |
| J | 28 | 29 |

Figure 30:
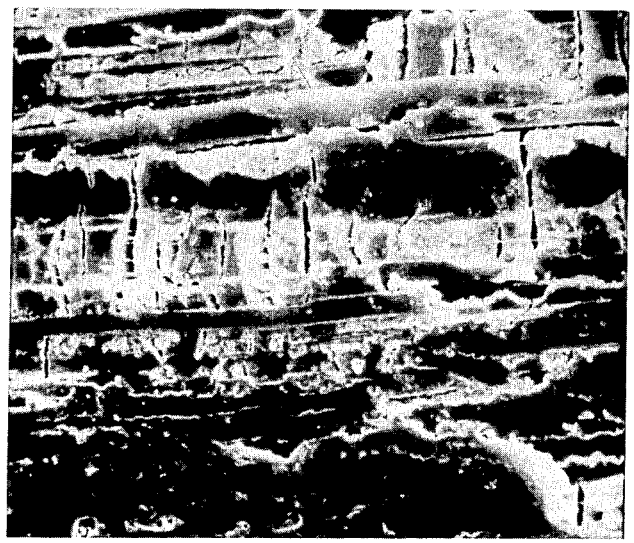
FIGS. 30–31 are photomicrographs of the surfaces of staples made from a blend of the invention after 14 days immersion in phosphate buffered saline at 37° C. One photomicrograph was taken at 1000× magnification and the other at 3000×.
Figure 31:
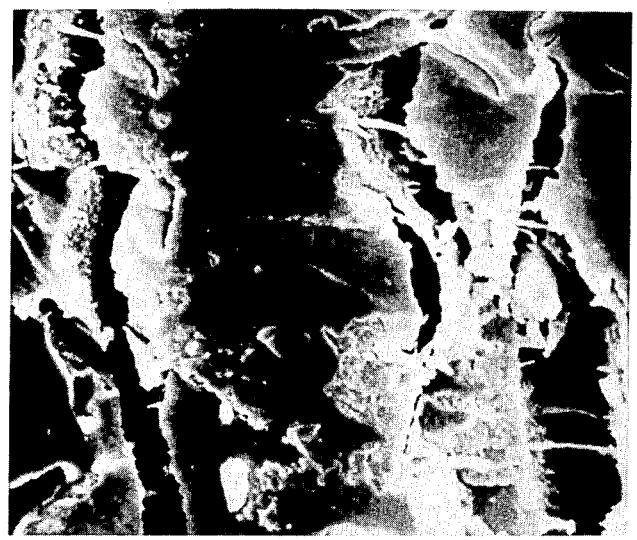

Also shown in the figures (FIGS. 30 and 31) are photomicrographs taken with an optical microscope of the surface of a molded staple portion of a surgical staple of the staple/receiver type (made from Blend A) after 14 days immersion in phosphate buffered saline at 37° C. One photomicrograph (FIG. 30) was taken at 1000× magnification and the other (FIG. 31) at 3000×. The initiation of absorption/degradation of the polymeric material in the blend is clearly seen as gaps or spaces. It is believed that the polyglycolide component of the blend is absorbed/degraded first.

EXAMPLES 4-7

A series of surgical fasteners of the staple/receiver type were molded by the procedure described above in Example 1 (except that the polymers constituting the blends of Examples 6 and 7 were melt blended and granulated prior to injection molding). The receivers were all made from polydioxanone and the staple portions were made from various blends of the invention. The fasteners were immersed in phosphate buffered saline, and the separation forces were measured after 0, 7, 14, 21, 28, 35, and 42 days, as described above in previous examples. The blend descriptions are the following:

Example 4–Blend of 15 parts by weight of PLA and 85 parts of PGA.

Example 5–Blend of 20 parts of PLA and 80 parts of PGA.

Example 6–Blend of 27 weight percent of an 85/15 L/G copolymer with 73 weight percent PGA, giving an overall L/G weight ratio in the blend of 23.7/76.3.

Example 7–Blend of 30 weight percent PLA and 85 weight percent PGA.

The table below presents the in vitro separation force data for annealed ("A") and unannealed ("U") staples made from the above blends. Each value given in the table is the average of ten tests.

Examples 4-7
Separation Force Data

| Example No. | Days in Vitro | | | | | | |
|---|---|---|---|---|---|---|---|
| | 0 | 7 | 14 | 21 | 28 | 35 | 42 |
| 4A | 8.78 | 1.96 | 0.50 | 0 | (1) | | |
| 4U | 9.53 | 0.99 | 0.57 | 0.16 | 0 | (1) | |
| 5A | 8.57 | 2.22 | 1.57 | 0.11 | 0(2) | (1) | |
| 5U | 9.77 | 1.57 | 0.84 | 0.30 | 0(1) | | |
| 6U(3) | 9.46 | 1.64 | 1.30 | 0.43 | 0.13 | 0.04* | 0 |
| 6U(4) | 8.72 | 1.86 | 0.97 | 0.36 | 0.12* | 0 | 0 |
| 6U(5) | 9.17 | 2.18 | 1.10 | 0.42 | 0.20* | 0.11 | 0 |
| 7U(3) | 9.19 | 1.56 | 1.53 | 0.57 | 0.38 | 0.32 | 0.16* |
| 7U(4) | 9.34 | 1.90 | 1.05 | 0.60 | 0.30 | 0.18* | 0.13 |
| 7U(5) | 8.32 | 1.80 | 1.44 | 0.66 | 0.30 | 0.23 | 0.15* |
| 7A(3) | 8.98 | 2.39 | 1.70 | 0.80 | 0.44 | 0.23* | 0.18 |
| 7A(4) | 8.32 | 2.44 | 1.52 | 0.64 | 0.34 | 0.21* | 0.09 |
| 7A(5) | 8.50 | 1.78 | 1.37 | 0.59 | 0.33 | 0.18* | 0.05 |

(1)Creamy.
(2)Soft.
(3)Mold temperature 20° C.
(4)Mold temperature 50° C.
(5)Mold temperature 110° C.
*Soft, fibrous.

The staples of Examples 4 and 5 that were annealed were annealed under nitrogen in three stages, 1 hour at 55° C., followed by 1 hour at 70° C., followed by 16 hours at 85° C. The staples of Example 7 were annealed at 60° C. for 16 hours.

What is claimed is:

1. A surgical fastener comprising a blend of at least two polymers, one of said polymers, which constitutes at least 50 weight percent of said blend, being polyglycolide homopolymer or a copolymer containing at least about 90 mole percent polymerized glycolide, the other of said polymers being polylactide homopolymer or a copolymer containing at least about 50 mole percent polymerized lactide, with the overall blend containing from about 65 to about 85 percent polymerized glycolide, wherein the fastener comprising said blend is impalpable after about six to ten weeks in vivo.

2. A surgical fastener in the form of a surgical staple comprising:
   (a) a staple member including a base member and at least one leg member terminating in a pointed free end, said leg member extending substantially perpendicularly from said base member; and
   (b) a receiving member including at least one aperture arranged and constructed to receive and retain the free end of said leg member,
wherein said staple member comprises a blend of at least two polymers, one of said polymers, which constitutes at least 50 weight percent of said blend, being polyglycolide homopolymer or a copolymer containing at least about 90 mole percent polymerized glycolide, the other of said polymers being polylactide homopolymer or a copolymer containing at least about 50 mole percent polymerized lactide, with the overall blend containing from about 65 to about 85 weight percent polymerized glycolide, wherein said receiving member comprises an absorbable polymer, wherein said surgical fastener has a measurable separation strength three weeks after implantation, and wherein the staple member is impalpable about six to ten weeks after implantation.

3. The surgical fastener of claim 2 wherein said absorbable polymer comprising said receiving member is poly(p-dioxanone).

4. The surgical fastener of claim 2 wherein said polyglycolide homopolymer or copolymer containing at least about 90 mol percent polymerized glycolide is polyglycolide homopolymer, wherein said polylactide homopolymer or copolymer containing at least about 50 mol percent polymerized lactide is a lactide/glycolide copolymer containing at least about 75 mol percent polymerized lactide, and wherein said blend contains from about 65 to about 85 weight percent of said polyglycolide homopolymer.

5. The surgical fastener of claim 3 wherein said polyglycolide homopolymer or copolymer containing at least about 90 mol percent polymerized glycolide is polyglycolide homopolymer, wherein said polylactide homopolymer or copolymer containing at least about 50 mol percent polymerized lactide is a lactide/glycolide copolymer containing at least about 75 mol percent polymerized lactide, and wherein said blend contains from about 65 to about 85 weight percent of said polyglycolide homopolymer.

6. The surgical fastener of claim 2 wherein the said other of said polymers is a lactide/glycolide copolymer containing at least about 75 mol percent lactide.

7. The surgical fastener of claim 1 wherein said other of said polymers contains at least about 65 mol percent of polymerized lactide.

8. The surgical fastener of claim 2 wherein said other of said polymers contains at least about 65 mol percent of polymerized lactide.

9. The surgical fastener of claim 1 wherein said other of said polymers contains at least about 75 mol percent of polymerized lactide.

10. The surgical fastener of claim 2 wherein said other of said polymers contains at least about 75 mol percent of polymerized lactide.

11. The surgical fastener of claim 1 wherein said other of said polymers contains at least about 85 mol percent of polymerized lactide.

12. The surgical fastener of claim 2 wherein said other of said polymers contains at least about 85 mol percent of polymerized lactide.

* * * * *

UNITED STATES PATENT AND TRADEMARK OFFICE
CERTIFICATE OF CORRECTION

PATENT NO. : 4,889,119
DATED : December 26, 1989
INVENTOR(S) : Dennis D. Jamiolkowski, Mark T. Gaterud, Hugh D. Newman, Jr., Shalaby W. Shalaby and Carl R. Smith It is certified that error appears in the above-identified patent and that said Letters Patent is hereby corrected as shown below:

Title page, item [75]: after "Lebanon," insert --Carl R. Smith, Medford,--;

Title page, the [*] Notice should indicate that the portion of the term of this patent "subsequent to" May 3, 2005 has been disclaimed.

Signed and Sealed this

Fifth Day of March, 1991

Attest:

HARRY F. MANBECK, JR.

*Attesting Officer*   *Commissioner of Patents and Trademarks*